US006831040B1

(12) United States Patent
Unkefer et al.

(10) Patent No.: US 6,831,040 B1
(45) Date of Patent: Dec. 14, 2004

(54) USE OF PROLINES FOR IMPROVING GROWTH AND OTHER PROPERTIES OF PLANTS AND ALGAE

(75) Inventors: Pat J. Unkefer, Los Alamos, NM (US); Thomas J. Knight, Portland, ME (US); Rodolfo A. Martinez, Santa Fe, NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/493,039

(22) Filed: Jan. 27, 2000

(51) Int. Cl.$^7$ .............................................. A01N 43/36
(52) U.S. Cl. ...................................................... 504/287
(58) Field of Search ........................................ 504/287

(56) References Cited

U.S. PATENT DOCUMENTS

| | | | | |
|---|---|---|---|---|
| 5,391,725 | A | 2/1995 | Coruzzi et al. | 536/24.1 |
| 5,561,236 | A | 10/1996 | Leemans et al. | 800/205 |
| 5,639,950 | A | 6/1997 | Verma et al. | 800/205 |
| 5,739,082 | A | 4/1998 | Donn | 504/206 |
| 5,840,656 | A | 11/1998 | Kinnersley et al. | 504/115 |

FOREIGN PATENT DOCUMENTS

| | | | |
|---|---|---|---|
| GB | 2097256 | * | 11/1982 |
| JP | 59080326 | | 5/1984 |
| JP | 63045211 | * | 2/1988 |

OTHER PUBLICATIONS

Stephen J. Temple et al., "Modulation of Glutamine Synthetase Gene Expression In Tobacco by the Introduction of an Alfalfa Glutamine Synthetase Gene in Sense and Antisense Orientation: Molecular and Biochemical Analysis", Mol. Gen. Genet 236, 424 (1997).

Remi Vincent et al., "Overexpression of a Soybean Gene Encoding Cytosolic Glutamine Synthetase in Shoots of Transgenic *Lotus coroniculatus* L. Plant Triggers Changes in Ammoium Assimilation and Plant Development", Planta 201, 424 (1997).

Peter Eckes et al., "Overproduction of Alfalfa Glutamine Synthetase in Transgenic Tobacco Plants", Mol. Gen. Genet. 217, 263 (1989).

Anis Limami et al., "Does Root Glutamine Synthetase Control Biomass Production in *Lotus japonicus* L.?", Planta 209, 495 (1999).

Alton Meister, "Enzymatic Preparation of α–Keto Acids", J. Biochem. 197, 304 (1952).

Bennett M. Shapiro and E. R. Stadtman, "Glutamine Synthetase (*E. coli*)", Meth. Enzym. 17A, 910 (1970).

Thomas J. Knight et al., "Oats Tolerant of *Pseudomonas syringae* pv. *Tabaci* Contain Tabtoxinine–β– Lactam–Insensitive Leaf Glutamine Synthetases", Plant Physiol. 88, 333 (1988).

Homer F. Daboll et al., "Mass Cultivation of Algae in Pure Heavy Water", Biotechnology & Bioengineering vol. IV pp. 281–297 (1962).

* cited by examiner

*Primary Examiner*—Alton N Pryor
(74) *Attorney, Agent, or Firm*—Bruce H. Cottrell

(57) ABSTRACT

Increasing the concentration of prolines, such as 2-hydroxy-5-oxoproline, in the foliar portions of plants has been shown to cause an increase in carbon dioxide fixation, growth rate, dry weight, nutritional value (amino acids), nodulation and nitrogen fixation, photosynthetically derived chemical energy, and resistance to insect pests over the same properties for wild type plants. This can be accomplished in four ways: (1) the application of a solution of the proline directly to the foliar portions of the plant by spraying these portions; (2) applying a solution of the proline to the plant roots; (3) genetically engineering the plant and screening to produce lines that over-express glutamine synthetase in the leaves which gives rise to increased concentration of the metabolite, 2-hydroxy-5-oxoproline (this proline is also known as 2-oxoglutaramate); and (4) impairing the glutamine synthetase activity in the plant roots which causes increased glutamine synthetase activity in the leaves which gives rise to increased concentration of 2-hydroxy-5-oxoproline. Prolines have also been found to induce similar effects in algae.

14 Claims, 4 Drawing Sheets

USE OF PROLINES FOR IMPROVING GROWTH AND OTHER PROPERTIES OF PLANTS AND ALGAE

STATEMENT REGARDING FEDERAL RIGHTS

This invention was made with government support under Contract No. W-7405-ENG-36 awarded by the U.S. Department of Energy to The Regents of The University of California. The government has certain rights in the invention.

FIELD OF THE INVENTION

The present invention relates generally to growth of plants and algae and, more particularly, to the use of the chemical class of compounds known as prolines for improving the properties and performance of plants and algae.

BACKGROUND OF THE INVENTION

Many agricultural activities are time sensitive, with costs and returns being dependent upon rapid turnover of crops or upon being first to reach the market place. Therefore, rapid plant growth is an economically important goal for many agricultural businesses that grow high-value crops such as vegetables, berries, and bananas, as well as for the greenhouse and nursery businesses. The importance of improved crop production technologies has increased as a result of the observation that yields for many well-developed crops have tended to plateau in recent years. The goal of rapid plant growth has been addressed in numerous studies of plant regulatory mechanisms, which remain incompletely understood. In particular, a complete understanding has not been attained for the plant regulatory mechanisms that coordinate carbon and nitrogen metabolism, which must have a major impact on plant growth and development.

The metabolism of carbon and nitrogen in photosynthetic organisms must be regulated in a coordinated manner to assure efficient use of plant resources and energy. Understanding of carbon and nitrogen metabolism now includes details of certain steps and metabolic pathways which are subsystems of larger systems. In photosynthetic organisms, carbon metabolism begins with $CO_2$ fixation which includes two major processes termed C-3 and C-4 metabolism. In plants with C-3 metabolism the enzyme, ribulose bisphosphate carboxylase (RuBisCo) catalyzes the combination of $CO_2$ with ribulose bisphosphate to produce 3-phosphoglycerate, a three carbon compound (C-3), that the plant uses to synthesize carbon-containing compounds. In plants with C-4 metabolism, $CO_2$ is combined with phosphoenol pyruvate to form acids containing four carbons (C-4) in a reaction catalyzed by the enzyme phosphoenol pyruvate carboxylase. The acids are transferred to the bundle sheath cells where they are decarboxylated to release the $CO_2$ which is then combined with ribulose bisphosphate in the same reaction as employed by C-3 plants. In photosynthetic organisms, nitrogen is assimilated by the action of the enzyme glutamine synthetase which catalyzes the combination of ammonia with glutamate to form glutamine.

Previous research focusing on important enzymes and the genes encoding for them has investigated the enzyme catalyzing the assimilation of nitrogen to form glutamine. One such study is "Modulation of Glutamine Synthetase Gene Expression In Tobacco by the Introduction of an Alfalfa Glutamine Synthetase Gene in Sense and Antisense Orientation: Molecular and Biochemical Analysis" by Stephen J. Temple et. al., Mol. Gen. Genet 236, 315 (1993), the teachings of which are hereby incorporated by reference herein. Therein it is stated that plants overexpressing the glutamine synthetase (GS) gene were visibly greener than control plants. Although, GS1-overexpressing plants exhibited about 45% increase in total soluble protein and the GS1 antisense expressing plants exhibited about 40% decrease in total soluble protein, no mention was made of more rapid growth rate or greater plant yields. In "Overexpression of a Soybean Gene Encoding Cytosolic Glutamine Synthetase in Shoots of Transgenic *Lotus coroniculatus* L. Plant Triggers Changes in Ammonium Assimilation and Plant Development" by Remi Vincent et. al., Planta 201, 424 (1997), it is stated that a 50% to 80% increase in total leaf GS activity in transgenic plants is followed by degradation of shoot protein and early floral development. As these properties are characteristic of senescent plants, Vincent et al. states that the over expression of GS in shoots may accelerate plant development, thus leading to premature flowering and early senescence. Again, no mention is made of any increase in plant yield or rate of growth. In "Overproduction of Alfalfa Glutamine Synthetase in Transgenic Tobacco Plants" by Peter Eckes et. al., Mol. Gen. Genet. 217, 263 (1989), the authors state that GS overproducing plants were fertile and grew normally, and that a high level of expression of a key metabolic enzyme such as glutamine synthetase does not interfere with growth and fertility of plants. No mention was made of the ratio of leaf-to-root GS activity, which has subsequently been measured by the present inventors to be approximately equal to that for wildtype plants although the activities in both the leaves and the roots have increased.

In "Does Root Glutamine Synthetase Control Plant Biomass Production in *Lotus Japonicus* L.?" by Anis Limami et al., Planta 209, 495 (1999), the authors show that over expression of root GS activity depresses biomass production. Two transgenic lines that were observed to grow poorly were investigated and the difference in growth between these lines is correlated with the amount of root GS activity; the poorest growth was responsive to the highest GS root activity. Leaf GS activity was observed to remain constant in the plants. Limami et al. do not describe a method for increasing biomass production or increasing plant growth rate or plant dry mass.

Numerous studies of nitrogen metabolism have found that various metabolites are important in the plants regulation of nitrogen metabolism. These compounds include the organic acid malate and the amino acids glutamate and glutamine. Two previous patents have been issued in this general area. In U.S. Pat. No. 5,840,656, for "Method for Increasing Fertilizer Efficiency" which issued to Alan Kinnersley et. al., on Nov. 24, 1998, an improved fertilizer composition is described that includes conventional fertilizers and an amino acid mixture which includes glutamic acid. U.S. Pat. No. 5,739,082 for "Method of Improving the Yield of Herbicide-Resistant Crop Plants" which issued to Gunter Donn on Apr. 14, 1998, reports the unexpected improvement in the yield of transgenic crop plants which have been engineered to be resistant to GS inhibitors resulting from the treatment of these plants with very low levels of GS inhibitors. The compound glufosinate [glufosinate-ammonium (ammonium DL-monalanin-4-yl-methyl phosphinate)] acts as a GS inhibitor because it is a structural analog of the GS substrate, glutamic acid. GS is responsible for the detoxification of $NH_3$, and when GS is inhibited by the glufosinate, the plant is severely damaged or destroyed by the toxic accumulation of $NH_3$. No mention is made of the ratio of leaf-to-root GS activity.

The compound, 2-hydroxy-5-oxoproline (also known as 2-oxoglutaramate) is synthesized and metabolized in plants by the sequential action of transaminase and hydrolyase enzymes. Similar transaminase and hydrolyase enzymes and the metabolite, 2-hydroxy-5-oxoproline, have been identified in animal livers and kidneys. These enzymes and the 2-hydroxy-5-oxoproline were partially characterized as described in "The Glutamine Transaminase-ω-Amidase Pathway" by Arthur L. Cooper and Alton Meister, CRC Critical Reviews in Biochemistry, pages 281–303 (January 1977), and "Enzymatic Preparation of α-Keto Acids" by Alton Meister, J. Biochem. 197, 304 (1952). However, no physiological function was attributed to these compositions in animals.

Accordingly, it is an object of the present invention to improve the properties of plants, including growth rate, fresh weight and dry weight, by increasing the effective quantity of compositions therein to positively affect these properties.

Additional objects, advantages and novel features of the invention will be set forth, in part, in the description that follows, and, in part, will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects of the present invention, and in accordance with its purposes, as embodied and broadly described herein, the composition hereof includes prolines in an amount effective to increase the rate of growth of plants and improve other properties of growing plants.

In another aspect of the present invention in accordance with its objects and purposes, the method for increasing the rate of growth of plants and for improving other properties of growing plants hereof includes contacting a plant with an effective amount of a proline.

It is preferred that the proline is applied to the foliar portion of the plant.

Preferably, a solution of 2-hydroxy-5-oxoproline (2-oxoglutaramate) is applied to the foliar portion of the plant.

Preferably also 2-hydroxy-5-oxoproline is applied at a rate sufficient to maintain an effective concentration of the proline in the leaf during the growing period of the plant.

Benefits and advantages of the present invention include significant improvement in plant properties, such as growth rate, nodulation, fresh weight and dry weight, with a simple and efficient plant treatment regimen. Similar effects have been observe for algae.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1a is a brief schematic representation of the biosynthesis of 2-hydroxy-5-oxoproline in the nitrogen assimilation process, and its relationship to carbon metabolism in a typical plant, while

DETAILED DESCRIPTION

Briefly, the present invention includes increasing the concentration of prolines in the foliar tissues of a plant to improve plant growth and other properties. This can be accomplished in four ways: (1) the application of a solution of the proline directly to the foliar portions of the plant by spraying these portions; (2) applying a solution of the proline to the plant roots; (3) genetically engineering the plant and screening to produce lines that over-express glutamine synthetase in the leaves which gives rise to increased concentration of the metabolite, 2-hydroxy-5-oxoproline (this proline is also known as 2-oxoglutaramate); and (4) impairing the glutamine synthetase activity in the plant roots which causes increased glutamine synthetase activity in the leaves which gives rise to increased concentration of 2-hydroxy-5-oxoproline.

Glutamine synthetase activity is a measure of the effectiveness of GS as a catalyst in the synthesis of glutamine and, ultimately, in the synthesis of 2-hydroxy-5-oxoproline. The present invention has been shown to raise the concentration of the 2-hydroxy-5-oxoproline in the foliar portions of treated plants which, as a consequence, have been observed to have better growth properties than untreated plants. That is, the treated plants exhibit greater fresh weight and percent dry weights and demonstrate an up-regulated carbon dioxide fixation rate with associated carbon metabolism, and a greater quantity of photosynthetically derived chemical energy than untreated plants as a result of the greater ratio of dry weight to fresh weight. The invention can be used to increase the economic value and return of agricultural crops. Additionally, prolines can be used as growth enhancers for greenhouse and other non-field growth environments. It should be mentioned at this point that not all plants of a chosen species are responders. It may be necessary to select plants which respond to increased foliar 2-hydroxy-5-oxoproline concentrations by observing their growth or other characteristics. Self-fertilized offspring of responding plants breed true. Prolines have been found to have a similar effect on algae.

Figure 1A:
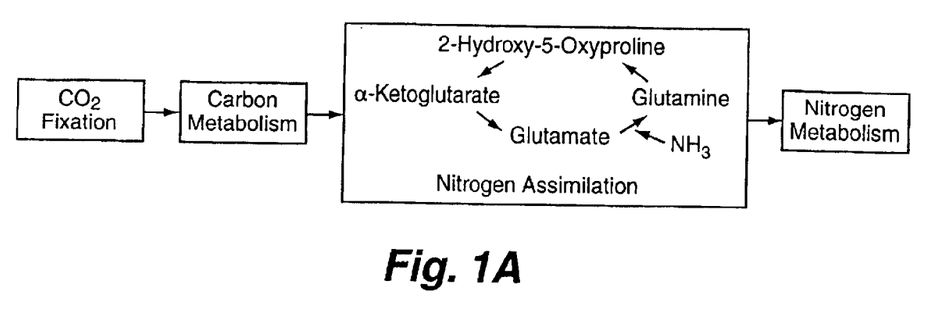

Reference will now be made in detail to the preferred embodiments of the present invention, examples of which are illustrated in the accompanying Figures. Coordination of carbon and nitrogen metabolism requires a mechanism for monitoring the two metabolic systems. The metabolite, 2-hydroxy-5-oxoproline has been identified in this monitoring process. It is believed by the present inventors that 2-hydroxy-5-oxoproline is made in a futile cycle in the plant. Futile cycles are short pathways with only a few steps that generate unusual and critical metabolites. Turning now to FIG. 1a hereof, it may be observed that this metabolite acts as a monitor of carbon or nitrogen flux through the main metabolic pathway. Thus, changes in the concentration of the 2-hydroxy-5-oxoproline are transmitted through signaling pathways and ultimately trigger changes in gene expression and consequently changes in metabolism. These characteristics of futile cycles are reflected in the creation and destruction of this metabolite and in the significant changes that occur in plants treated with exogenous 2-hydroxy-5-oxoproline as will be demonstrated hereinbelow.

Also shown in FIG. 1a hereof, plants catalyze the conversion of glutamine to synthesize 2-hydroxy-5-oxoproline through the action of a transaminase enzyme. Thus, the concentration of 2-hydroxy-5-oxoproline is linked to the concentration of glutamine in the plant, assuming the rate of destruction of this compound through a hydrolyase activity which removes the amide nitrogen of the 2-hydroxy-5-oxoproline and converts it to α-ketoglutarate, is approximately constant. The 2-hydroxy-5-oxoproline, has been shown to be present in plant leaves and the synthetic activity of the transaminase enzyme is capable of generating the observed concentrations of 2-hydroxy-5-oxoproline.

Figure 1B:
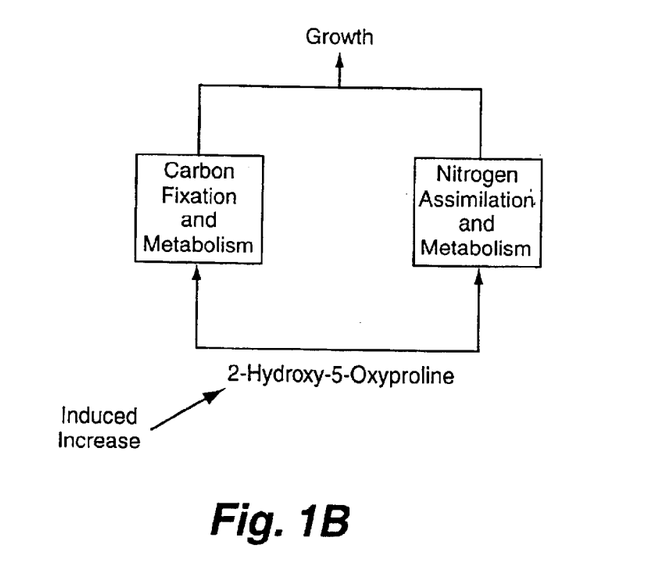
FIG. 1b is a simplified schematic of the regulatory function of the 2-hydroxy-5-oxoproline in the carbon metabolism and nitrogen assimilation processes in a typical plant in order to illustrate the changes in the foliar concentration thereof affects plant growth.

FIG. 1b shows schematically that since the concentration of 2-hydroxy-5-oxoproline is linked to the concentration of glutamine, increased glutamine concentration results in the generation of additional 2-hydroxy-5-oxoproline which promotes growth by simultaneously coordinating carbon fixation and metabolism and nitrogen assimilation and metabolism. In order for this process to result in plant growth, an increase in the concentration of 2-hydroxy-5-oxoproline in the leaves is required. A number of progeny of plants which over express the GS gene (transgenic) have been found to grow rapidly. These plants are observed to contain an increased ratio of leaf-to-root GS activity, and an increased GS activity in the leaves which results in an increased concentration of 2-hydroxy-5-oxoproline in the leaves. Another way to accomplish the improved growth is by direct foliar treatment of the plant with 2-hydroxy-5-oxoproline, or by sufficient quantities of this metabolite being applied to the plant roots to allow for translocation to the leaves of the effective quantity.

It will be shown that when plants are grown in the presence of 2-hydroxy-5-oxoproline, the compound is taken up through the roots and transported to the leaves. Alternatively, plants may be treated by application of a solution of 2-hydroxy-5-oxoproline to the foliar portions thereof. Since prolines are readily degraded by commonly occurring microbes, foliar treatment is expected to be more economical and efficient. Treated plants have been found to contain elevated levels of the compound. Oats, alfalfa, tomato, cantaloupe, cotton and lettuce, all C-3 Plants; and switchgrass, a C-4 Plant, were chosen as representatives of the major plant groups based on their carbon-fixation metabolism, and were treated with 2-hydroxy-5-oxoproline. Overall plant growth and other growth-related indicia such as plant fresh weight and plant dry weight were monitored.

The immediate effects of increases in plant foliar 2-hydroxy-5-oxoproline concentrations may be monitored by observing increased $CO_2$ fixation rates. Plants having increased $CO_2$ fixation rates were found to exhibit increased growth rates, while as the level of 2-hydroxy-5-oxoproline diminishes, these functions were also found to diminish. Effective treatment dose is species dependent, and may also be determined by monitoring the growth of the treated plants, for example, by visual inspection or weighing the plants, and comparing these results with those for untreated plants. Effective treatment doses have tended to be lower for foliar application, because increasing the concentration in the foliar tissues has been observed to be essential to the plant response. Single treatments and periodic treatments during plant growth have been undertaken. The treatment frequency or schedule employed depends upon the plant species and upon the goals of the user. Possible goals include faster growth during a specific phase of the plant's life such as early growth in a greenhouse to allow for faster transplanting of plants while requiring less time in the greenhouse, helping to overcome transplant shock for plants, or faster growth sustained in the field, nursery, or greenhouse. A single treatment was sufficient to produce increased growth rate in cantaloupe and cotton seedlings.

Figure 2:
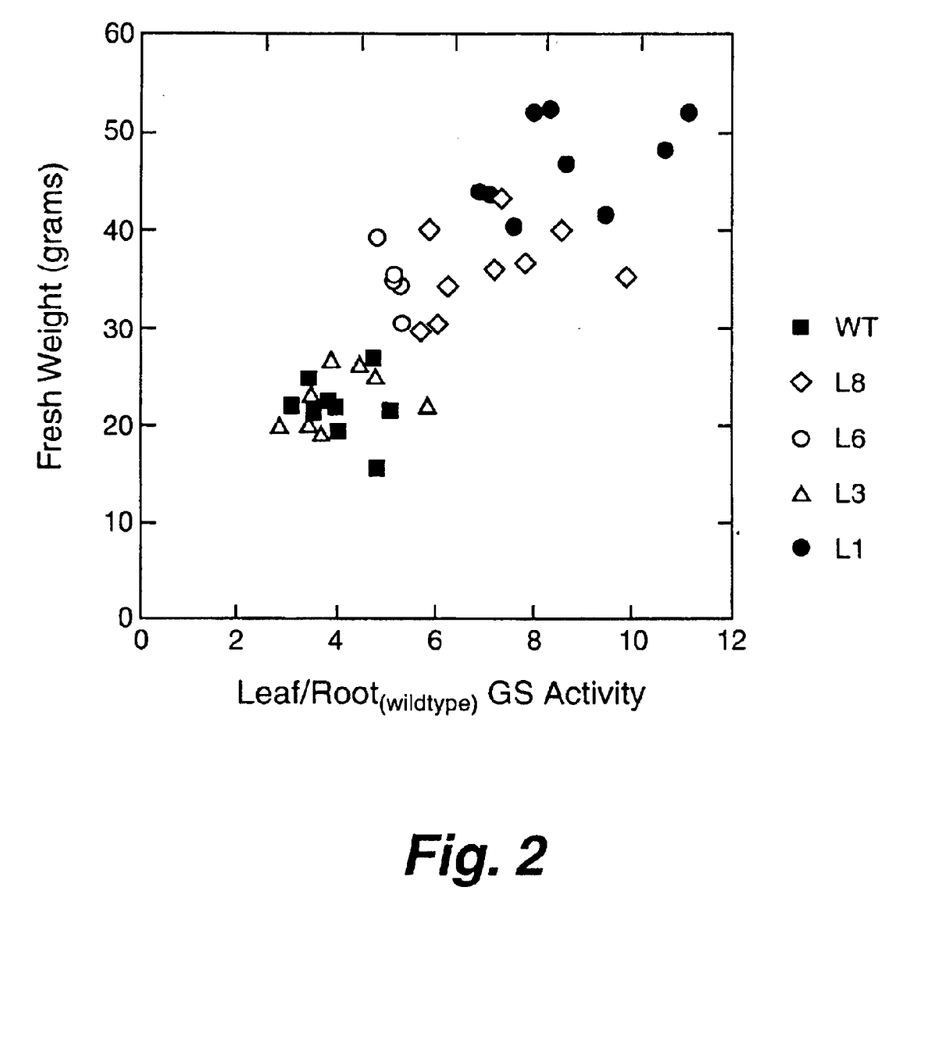
FIG. 2 shows the fresh weight of plants as a function of the ratio of the leaf/root$_{(wildtype)}$ glutamine synthetase activity for wild type and four transgenic lines (lines 1,3,6, and 8) of tobacco, and illustrates that not all of the transgenic plant lines have the desired properties.

Transgenic plant lines genetically engineered to over express GS in their foliar portions (while GS in the root portions were normal or impaired) were found to produce increased 2-hydroxy-5-oxoproline levels in their foliar portions, which was found to lead to markedly increased growth rates over wildtypes; root GS activity is approximately that of the wildtype (unaltered) plants for these plants. FIG. 2 shows the ratio of the leaf/root glutamine synthetase activity for wildtype and for four transgenic tobacco plant lines, and illustrates that not all of the transgenic plant lines have the desired properties. The transgenic plants were allowed to self-fertilize (selfing) to permit genetic segregation and produce offspring having increased numbers of copies of the glutamine synthetase transgene to increase expression of GS activity in the leaf tissues while allowing essentially normal or impaired GS activity in the root tissues of the same plants. These are the plants that exhibit increased growth rate and improved plant properties, while those plants which have been genetically engineered to over express GS and which have not been screened and genetically segregated by selfing or cross pollinating do not exhibit an increased leaf-to-root GS activity ratio and do not present improved properties. Therefore, plants must be selected for increased growth and genetically segregated by selfing as an example with continued selection until a line breeds true (genetically homozygous for the desired trait), so that the trait is expressed in all offspring in subsequent generations.

Figure 3:
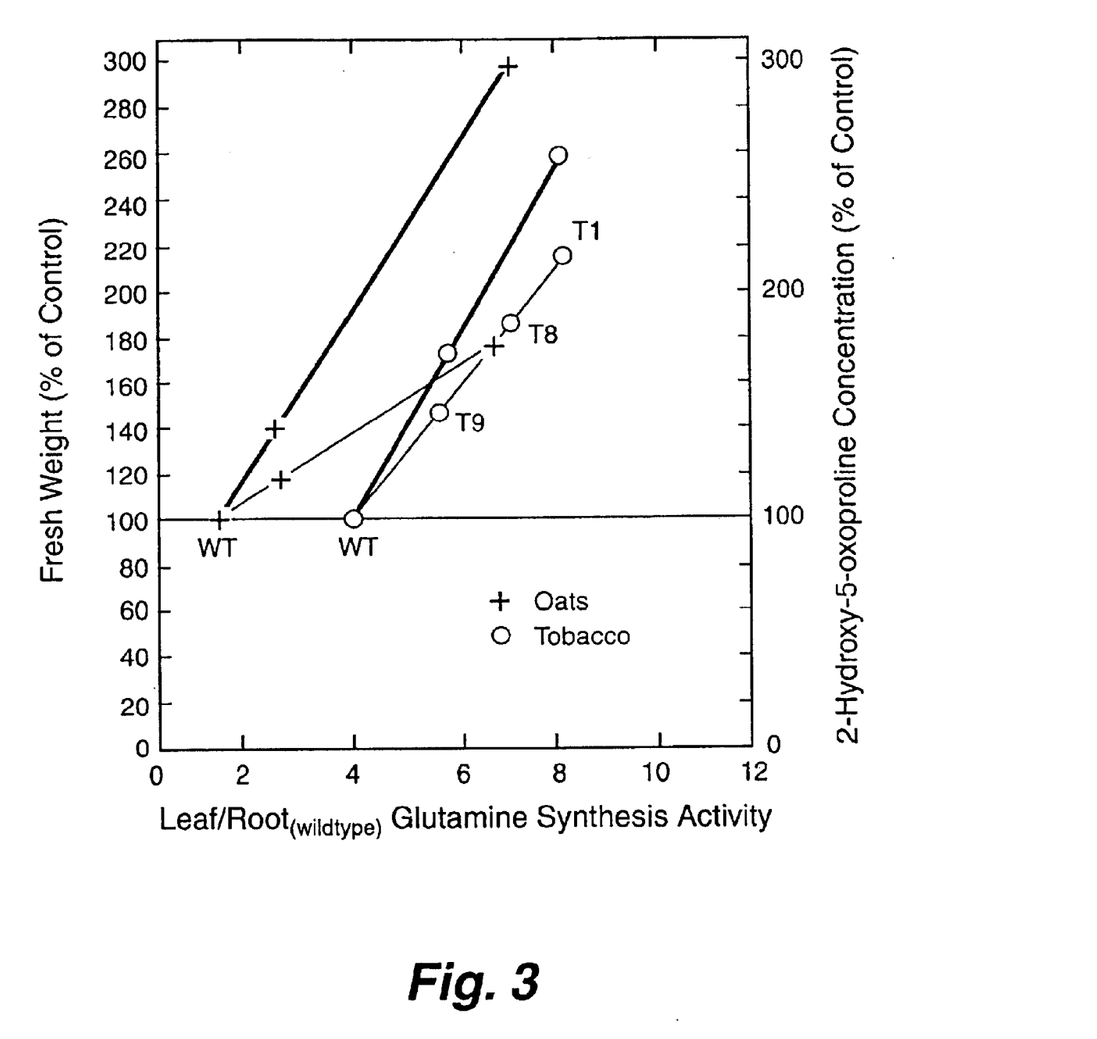
FIG. 3 is a graph showing the foliar concentration of 2-hydroxy-5-oxoproline (thick lines) in oats (x's) treated with this compound and in transgenic tobacco plants (open circles) and the fresh weights (FWT) of these plants (thin lines), plotted as a function of the ratio of their leaf/root$_{(wildtype)}$ GS activity.

FIG. 3 is a graph illustrating the foliar concentration of 2-hydroxy-5-oxoproline expressed as a percentage of that in control plants (thick lines) for oats (x's) treated with 2-hydroxy-5-oxoproline and for transgenic tobacco plants (open circles), and the fresh weight percent for the treated oat plants and transgenic tobacco plants expressed as a percentage of that for control plants (thin lines), both as a function of leaf/root ratio of GS activity. The root GS activity is that of the wildtype (unaltered) plants. It may be observed that increased leaf/root GS concentration ratios yield greater concentrations of 2-hydroxy-5-oxoproline in the leaves and greater fresh weights.

A dramatic increase in growth rate of algae growing photosynthetically has been observed when treated with 2-hydroxy-5-oxoproline. Continuously culturing the algae in the presence of this compound or mixtures of this compound with other prolines will enrich sub-strains of the algae that respond well to the prolines.

Having generally described the invention, the following EXAMPLES provide additional details of the effects of the metabolite, 2-hydroxy-5-oxoproline and other prolines on plant properties. In the EXAMPLES, the concentration of 2-hydroxy-5-oxoproline in plant leaves was determined by extracting the 2-hydroxy-5-oxoproline into acidified water from a known weight of fresh leaf tissue. The sampled leaves were fully extended and photosynthetically active. The amount of 2-hydroxy-5-oxoproline was measured using a high-performance liquid chromatograph fitted with an optical detector (210 nm) and a column packed with a sulfonated polystyrene di-vinyl benzene polymer suitable for ion-exclusion chromatography of Kreb cycle intermediates. The metabolite was eluted with 0.01N $H_2SO_4$ in water. The chromatograph peak corresponding to 2-hydroxy-5-oxoproline was identified by the known column retention time of 2-hydroxy-5-oxoproline. A standard curve was prepared using chemically synthesized 2-hydroxy-5-oxoproline (structure confirmed using 13-C nuclear magnetic resonance) and varying the amount of this standard injected into the system. The area integrated under the peak was correlated with the known amount of standard injected into the chromatograph. The amount of 2-hydroxy-5-oxoproline in leaf tissue samples could then be quantitatively determined from the area under the appropriate peak.

Glutamine synthetase activity was measured using the transferase assay as described in "Glutamine Synthetase (*E. coli*)" by B. Shapiro and E. Stadtman, Meth. Enzym. 17A, 910 (1970). The GS activity is expressed in micromoles per gram of fresh weight of tissue per minute.

Also in the EXAMPLES, plants were grown at 73° F. with 16 h length days and 8 h length nights. Fluorescent lights were supplemented with incandescent bulbs to generate intensities of 1760, 980 or 360 microeinsteins per meter squared per second as indicated in the EXAMPLES. Plants were grown in a standard potting mixture of peat moss, vermiculite and perlite, and nutrients were supplied by watering daily with the commonly used Hoagland's plant nutrient solution which contains an array of known plant nutrients and is considered to be appropriate to meet the nutrient needs of plants as they normally receive them from soil.

Transgenic lines were created as described in Temple et al., supra. The plants in each of these lines were allowed to self-fertilize in at least the T-0, and T-1, generations. Self-fertilization was performed to permit genetic segregation to produce offspring with increased numbers of copies of the glutamine synthetase transgene to increase expression of glutamine synthetase activity in the leaf tissues and to allow for other molecular or genetic events to either maintain essentially normal or impaired glutamine synthetase activity in the root tissues of the same plants. Therefore, plants must be selected for increased growth and reproduced by selfing with continued selection until a line breeds true. This screen for increased growth was done among and within the various transgene lines. The seeds of each of the generations were germinated on Murashige and Skoog medium containing kanamycin. The presence of kanamycin in the medium permitted the identification of and the screening of the transgenic plants resulting from each generation. The seeds from the T-1 generation, the T-2 generation, were thus germinated and grown to young plants. The ratio of leaf/root glutamine synthetase was then determined by sampling the leaves and roots of these T-2 generation plants and measuring the glutamine synthetase activities.

In the practice of the present invention, plants were treated regularly in order to sustain increased $CO_2$ fixation and increased metabolic rates by directly measuring the $CO_2$ fixation rate repeating treatment when this rate declines. Multiple treatments over several weeks were found to give the best plant growth, development, and the most improved related physiological parameters.

The concentrations of 2-hydroxy-5-oxoproline set forth in Tables 1, 2, 5, and 6, hereinbelow, show the concentrations of this material in the plant leaves.

Turning now to the EXAMPLES:

EXAMPLE 1
Daily Root Treatment of Oats (C-3 Plant) with 2-hydroxy-5-oxoproline TABLE 1 shows the results of harvesting oat plants (C-3 Plant) (commercial cultivar Lodi) whose roots were treated daily with 2-hydroxy-5-oxoproline. The treatment was commenced when the seedlings were 7 days old and continued for 56 days; the 2-hydroxy-5-oxoproline was supplied daily to their roots as 50 ml of between 0.5 to 50 μM solutions of 2-hydroxy-5-oxoproline in Hoagland's plant nutrient solution having a pH of 6.3. Oats treated with 2-hydroxy-5-oxoproline contained higher percent dry weight than did controls. When the amount of dry weight was expressed as a function of fresh weight, the percent dry weight of the treated plants ranged from 8.1 to 8.4% when compared with 7.6% for untreated control plants.

TABLE 1

| Parameter/ Plant | Whole Plant Fresh Weight (FWT), g | 2-Hydroxy-5-oxoproline Concentration in Leaf (micromoles/gFWT) |
| --- | --- | --- |
| Control | 14.95 | 4.9 |
| Treated | 18.06 | 7.0 |

EXAMPLE 2
Weekly Foliar Treatment of Lettuce (C-3 Plant) with 2-hydroxy-5-oxoproline TABLE 2 shows the results for lettuce (a C-3 Plant) where treatment was initiated with 7-day old plants. The fresh weight, dry weight, percent dry weight, 2-hydroxy-5-oxoproline concentration in the leaves, and the $CO_2$ fixation rates are all increased in the treated plants. The greater dry weight percent increases the value of these plants and that of algae as fuel because the increase provides a greater amount of combustible material per gram of fresh weight (that is, a greater amount of carbon was fixed by the plant), and because an increase in dry weight percent reduces the water content in the fuel which is an energy cost when the fuel is combusted. It also increases the value of these plants as sources of biomass suitable for conversion to other products such as chemicals, liquid fuels, or hydrogen, to name a few examples. Treatments were applied weekly to the foliar parts of the plants using an air brush until approximately 20% drip. The aqueous treatment solution contained 2-hydroxy-5-oxoproline (10 mg/liter) in 0.07% sodium laurel sulfate, and 1.2% glycerol at a pH of 6.3. The plants were harvested at 63 days of age after 7 treatments; the harvest was made 7 days after the last treatment. These plants were provided Hoagland's plant nutrient solution to their roots and grown under light intensity of 380 microeinsteins.

TABLE 2

| Parameter/ Plant | Whole Plant Fresh Weight (FWT) g | Whole Plant Dry Weight (DW) g | 2-Hydroxy-5-oxoproline Concentration in Leaf (micromoles/ gFWT) | $CO_2$ Fixation Rate (micromoles $CO_2$ fixed/m²/sec) |
| --- | --- | --- | --- | --- |
| Control | 55.3 [100%] | 4.00 [100%] | 6.25 [100%] | 6.6[a], 6.9[b] |
| Treated | 65.2 [118%] | 6.35 [159%] | 13.37 [212%] | 9.0[a], 9.6[b] |

[a]34 day-old, and
[b]57 day-old plants

At harvest (63 days of age) none of the 12 control plants had emerged flowering structures, whereas 6 of the 12 treated plants had well-developed flowering structures.

EXAMPLE 3
Daily Root Treatment of Alfalfa (C-3 Plant) with 2-hydroxy-5-oxoproline TABLE 3 shows the results of treatment of alfalfa plants (a C-3 Plant) with 2-hydroxy-5-oxoproline. Growth and nodulation were improved by the treatment. The alfalfa commercial cultivar Saranac, was grown as described hereinabove using 1760 microeinsteins per meter squared per second as the light intensity, and watered daily with quarter-strength Hoagland's plant nutrient solution that had been modified to replace the nitrogen (nitrate) with chloride in the solution. Nodulating alfalfa seedlings were treated beginning at about 4 days of age, with the same quantity of 2-hydroxy-5-oxoproline as described in EXAMPLE 1 for plants receiving the 2-hydroxy-5-oxoproline through their roots.

TABLE 3

| Plants | Whole plant Fresh weight (%) | Nodule number/ plant (%) | Nodule weight/ plant (%) |
|---|---|---|---|
| Controls | 100 | 100 | 100 |
| Treated (soil) | 145 | 214 | 165 |

The time to flowering or emergence of seed structures of treated daily and untreated plants was tracked in alfalfa and oats. The treated alfalfa plants flowered 2–5 days sooner than did the untreated plants, while the treated oat plants displayed seed structures 3–5 days earlier than did the untreated control plants.

Figure 4:
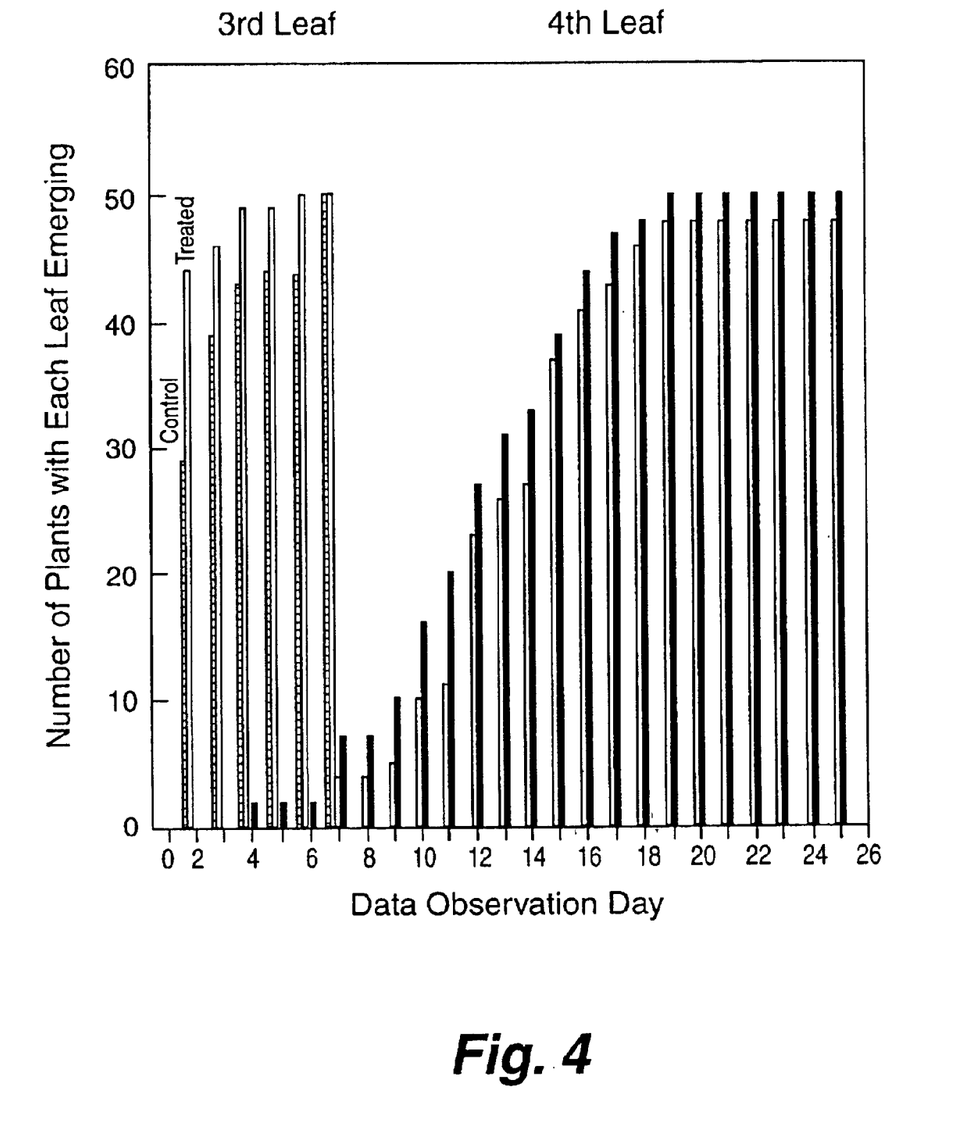
FIG. 4 is a graph showing the emergence of the $3^{rd}$ and $4^{th}$ leaves for switchgrass treated with 2-hydroxy-5-oxoproline, versus that for untreated switchgrass plants, as a function of time.

EXAMPLE 4
Daily Root Treatment of Switchgrass (C-4 Plant) with 2-hydroxy-5-oxoproline Switchgrass (a plant with C-4 metabolism, commercial cultivar, Alamo) plants were treated with 2-hydroxy-5-oxoproline and when harvested had grown better than had controls and as such treated plants had greater fresh weights than controls and also had a higher content of dry weight when expressed per unit of fresh weight. Average fresh weight of the foliar part of the plants was 115% of that for the control plants. The dry weight was increased in these plants (16.5% and 12.05% in foliar parts and roots, respectively) in such a manner to provide a greater amount of fixed carbon per unit of fresh weight than untreated plants (14.9% and 6.7% in foliar parts and roots, respectively. The plants were treated as described in EXAMPLE 1 and grown as described in the preceding section under 1760 microeinsteins per meter squared per second of light intensity, and the plants were harvested and the fresh weights measured. The better growth of the treated plants is further demonstrated by tracking the emergence of specific leaves in treated and control plants as shown in FIG. 4 which shows the treated switchgrass plants consistently emerged leaves sooner than did the control plants.

EXAMPLE 5
Daily Root Treatment of Oats (C-3 Plant) with 2-hydroxy-5-oxoproline; Selection of Responders TABLE 4 shows the results of screening a population of wildtype oats (commercial cultivar Lodi) for those plants which respond to treatment with 2-hydroxy-5-oxoproline applied through their roots. Oats were treated with 2-hydroxy-5-oxoproline through their roots as described in EXAMPLE 1. Individual plants that responded to the increased level of 2-hydroxy-5-oxoproline were identified by measuring the rate of $CO_2$ fixation using a $CO_2$ fixation meter at the maximum light intensity for photosynthetic carbon dioxide fixation of 2000 microeinsteins per meter squared per second. The rates were measured in the leaves of treated plants on two successive days and the plants were allowed to mature and produce seed. Other parameters of rapid growth such as number of tillers or rate of leaf emergence were also useful in choosing a population of plants that had a greater fraction of members which respond to 2-hydroxy-5-oxoproline treatment. The progeny of this selection were found to maintain the response trait.

TABLE 4

| Individual Plant | $CO_2$ fixation Rate as Differential $CO_2$ Concentration, ppm | Number of Tillers in Mature Plant |
|---|---|---|
| Treated Plants | | |
| Responders | 28.9 | 13 |
| | 28.0 | 18 |
| | 25.9 | 17 |
| | 25.3 | 17 |
| | 25.2 | 21 |
| | 24.5 | 19 |
| | 24.2 | 12 |
| | 24.2 | 15 |
| | 23.6 | 21 |
| | 23.2 | 17 |
| Average of Responders | 25.3 | 17.0 |
| Non-Responders | 19.9 | 14 |
| | 19.6 | 13 |
| | 17.2 | 15 |
| | 16.1 | 14 |
| Average of Non-Responders | 18.2 | 14.0 |
| Untreated Plants | 18.9 | 14 |
| | 16.9 | 14 |
| | 18.9 | 13 |
| Average of Untreated Plants | 18.2 | 13.7 |

EXAMPLE 6
Daily Root Treatment of Oats (C-3 Plant) with 2-hydroxy-5-oxoproline; Effects of Increasing Leaf/root GS Ratio TABLE 5 and FIG. 3 hereof show the results of increasing the ratio of leaf/root GS activity on plant growth and on the concentration of 2-hydroxy-5-oxoproline in the leaves of oat plants treated with a compound (tabtoxinine-β-lactam) that binds to glutamine synthetase and impairs the normal destruction of this enzyme, thereby causing the leaf GS activity to increase while the root GS activity decreases. (For methodology, see, e.g., T. Knight, D. Bush, and P. Langston-Unkefer, Plant Physiol. 88, 333 (1988)). The compound (Tabtoxinine-β-lactam) was delivered to the roots. The plants were found to grow rapidly and outgrew oats not treated. When allowed to grow without treatment, the oats grow at normal rates and were observed to contain the same ratio of leaf/root GS ratio that is found in the wildtype oats. The treated, rapidly growing oats were observed to have sharply increased GS activity in their leaves and diminished glutamine synthetase in the roots; thus these plants had an increased leaf/root GS ratio. The level of 2-hydroxy-5-oxoproline was also observed to increase in the leaves of these plants as a consequence of the increased leaf/root GS activity ratio.

TABLE 5

| Treatment Of Oats | Whole Plant Fresh Weight (FWT) (g) | GS Activity (micromoles/g FWT/min) | Leaf/Root GS Activity Ratio | 2-Hydroxy-5-oxoproline in Leaf (micromoles/g FWT) |
|---|---|---|---|---|
| Controls | 14.95 | Leaf: 10.5<br>Root: 7.8 | 1.35 | 4.9 |
| Tabtoxinine-β-lactam-treated oats | 24.6 | Leaf: 25.9<br>Root: 3.9 | 6.6 | 16.6 |
| 2-Hydroxy-5-oxoproline treated Oats | 18.07 | Leaf: 16.9<br>Root: 6.4 | 2.64 | 7.04 |

EXAMPLE 7
Genetically Increasing the Leaf/root GS Ratio in Tobacco Plants

TABLE 6 shows the results of genetically increasing the ratio of leaf/root glutamine synthetase activity on plant growth and level of 2-hydroxy-5-oxoproline in the plants. Transgenic lines of tobacco containing an increased ratio of leaf/root glutamine synthetase activity were screened for in the T-2 generation. The screening was done by measuring the activity of glutamine synthetase in the leaf and root tissues of plants and determining the ratio of leaf/root glutamine synthetase activity. Plants having increased leaf/root GS ratio grew at faster rates than did their counterparts with the normal ratio of leaf/root GS ratio as shown in TABLE 6. See also FIG. 2 hereof.

TABLE 6

| Plant Treatment | Whole Plant Fresh Weight (FWT) (g) | GS Activity (micromoles/g FWT/min) | Leaf/Root GS Activity Ratio | 2-Hydroxy-5-oxoproline in Leaf (micromoles/g FWT) |
|---|---|---|---|---|
| Control | 21.8 | Leaf: 24.0<br>Root: 6.3 | 3.9 | 6.0 |
| Line 1 | 46.8 | Leaf: 43.1<br>Root: 5.1 | 8.6 | 16.1 |
| Line 8 | 36.1 | Leaf: 32.6<br>Root: 4.7 | 6.9 | 9.7 |

EXAMPLE 8
Effects of 2-hydroxy-5-oxoproline on Algae

The growth rate of algae, *Chlorella sorokinian* (obtained from the American Type Culture Collection), was increased when 2-hydroxy-5-oxoproline was added to the growth medium. The mass accumulation growth curve for this single-cell photosynthetic organism is described as a sigmoidal function. The time it takes to reach the mid-log phase of growth was substantially reduced for treated algae (approximately 40 h) when compared with untreated algae (approximately 60 h). This reflects substantially accelerated growth for the treated algae cultures when compared with untreated cultures. The growth medium for algae growth is described in Biotechnology & Bioengineering Vol. IV by Daboll et al., pages 281–297 (1962). Carbon dioxide was provided as the sole carbon source and was allowed to sparge into the cultures of both treated and untreated cultures. The light source supplied approximately 980 ft candles. Media pH was initially adjusted to 8.0 using either NaOH or HCl, and subsequently maintained at pH 7.0 by controlling the introduction of $CO_2$.

EXAMPLE 9
Foliar Treatment of Oats (C-3 Plant) with 5-oxoproline (2-pyrrolidone-5-carboxylic Acid)

Foliar treatment of oat plants with the structural analog of 2-hydroxy-5-oxoproline, 5-oxoproline (2-pyrrolidone-5-carboxylic acid) also resulted in increased plant growth rate. The treated plants were found to yield fresh foliar weights that were 126% of the foliar weights for untreated control plants when harvested 17 days after the single treatment. A solution containing 40.5 mg per milliliter of 2-pyrrolidone-5-carboxylic acid and 1% dimethylsulfoxide in water at a pH of 6.3 was applied, but other solutions of this compound were also found to be effective. These plants were grown under lights of 980 microeinsteins per meter squared per second and the treatment was applied to their foliar parts.

EXAMPLE 10
Daily Root Treatment of Alfalfa (C-3 Plant) with 2-hydroxy-5-oxoproline; Effect on Insect Infestation Plants having increased 2-hydroxy-5-oxoproline concentration were found to have fewer insect pests infesting them than did the control plants. Thrip infestation of plants having increased 2-hydroxy-5-oxoproline concentration was compared with that of control plants having a normal level of 2-hydroxy-5-oxoproline in their leaves. Control (80 Plants) and plants with elevated levels of 2-hydroxy-5-oxoproline (80 Plants) were subjected to thrip infestation; these two sets of plants were randomly intermingled in the greenhouse to assure equal exposure to the pest. Of the set of control plants, 15 were infested with thrip while only 11 of the other set of plants were infested with thrip one week after initial exposure to the pests. The light intensity for growth was approximately 1760 microeinsteins per meter squared per second.

EXAMPLE 11
Single or Multiple Foliar Treatment of Other Plants with 2-hydroxy-5-oxoproline TABLE 7 and TABLE 8 show the results when commercial vegetables such as cantaloupe, and tomatoes, and a crop such as cotton were tested for the effects of the metabolite on their growth rates. These plants received one foliar application of 2-hydroxy-5-oxoproline as young seedlings. These plants grew more rapidly as determined by either fresh weight or leaf length. The cantaloupe and cotton seedlings were harvested and their fresh weight was determined.

TABLE 7

| Plant and Variety | Foliar Fresh Weight, g Untreated plants | Foliar Fresh Weight, g Treated plants |
|---|---|---|
| Cantaloupe-Imperial | 0.85 | 1.55* |
| Cotton-Pima | 1.27 | 1.85* |
| Tomato-Halley 3155 | 11.97** | 19.08** |

*Plants were 16 days old and were harvested 9 day after the treated plants had received a single treatment.
**Plants were 24 days old and treated plants had received 5 weekly treatments.

The foregoing description of the invention has been presented for purposes of illustration and description and is not intended to be exhaustive or to limit the invention to the precise form disclosed, and obviously many modifications and variations are possible in light of the above teaching. For example, plants may be treated with prolines by injection of these materials into plant stems, pseudo stems or trunks. Moreover, because increasing the leaf concentration of 2-hydroxy-5-oxoproline has been shown to lead to improved growth and other plant properties, other genetic methods might be employed for increasing the foliar concentration of 2-hydroxy-5-oxoproline; among them: (1) the over expression of the transaminase gene followed by screening for improvements in plant properties; and (2) impairment of the amidase gene which assists in the removal of 2-hydroxy-5-oxoproline from the cells, followed by screening for improvements in plant properties.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for increasing the rate of growth of plants over that for a wild type plant, comprising contacting said plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

2. A method for increasing the rate of growth of plants over that for a wild type plant, comprising contacting said plant with an effective amount of a proline or a mixture of prolines, further comprising the steps of screening the plants contacted with an effective amount of a proline or a mixture of prolines for those plants which demonstrate a strong growth response to contact with said effective amount of said proline or said mixture of prolines therewith, and genetically segregating the screened plants, thereby producing strains of plants which exhibit a strong growth response when contacted with the effective amount of the proline or the mixture of prolines therewith.

3. A method for increasing plant nodulation over that for a wild type plant, comprising contacting said plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

4. A method for increasing plant nodulation over that for a wild type plant, comprising contacting said plant with an effective amount of a proline or a mixture of prolines, further comprising the steps of screening the plants contacted with an effective amount of a proline or a mixture of prolines for those plants which demonstrate increased nodulation in response to contact with said effective amount of said proline or said mixture of prolines therewith, and genetically segregating the screened plants, thereby producing strains of plants which exhibit an increase in nodulation in response to contact with the effective amount of the proline or the mixture of prolines therewith.

5. A method for increasing the percent dry weight of a plant over that for a wild type plant, comprising contacting said plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

6. A method for increasing the percent dry weight of a plant over that for a wild type plant, comprising contacting said plant with an effective amount of a proline or a mixture of prolines, further comprising the steps of screening the plants contacted with the effective amount of the proline or the mixture of prolines for those plants which demonstrate an increase in percent dry weight in response to contact with the effective amount of the proline or a mixture of prolines therewith, and genetically segregating the screened plants, thereby producing strains of plants which exhibit an increase in percent dry weight in response to contact with the effective amount of the proline or the mixture of prolines therewith.

7. A method for increasing the fresh weight of plants over that for wild type plants, comprising contacting said plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

8. A method for increasing the fresh weight of plants over that for wild type plants, comprising contacting said plant with an effective amount of a proline or a mixture of prolines, further comprising the steps of screening the plants contacted with the effective amount of the proline or the mixture of prolines for those plants which demonstrate an increase in fresh weight in response to contact with the effective amount of the proline or the mixture of prolines therewith, and genetically segregating the screened plants, thereby producing strains of plants which exhibit an increase in fresh weight in response to contact with the effective amount of the proline or mixture of prolines therewith.

9. A method for improving plant resistance to insect pests over that for a wild type plant, comprising contacting said plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

10. A method for improving plant resistance to insect pests over that for a wild type plant, comprising contacting said plant with an effective amount of a proline or a mixture of prolines, further comprising the steps of screening the plants contacted with the effective amount of the proline or the mixture of prolines for those plants which demonstrate improved resistance to said insect pests in response to contact with the effective amount of the proline or the mixture of prolines therewith, and genetically segregating the screened plants, thereby producing strains of plants which exhibit improved resistance to said insect pests in response to contact with the effective amount of the proline or the mixture of prolines therewith.

11. A method for improving plant resistance to insect pests over that for a wild type plant, comprising contacting said plant with an effective amount of a proline or a mixture of prolines, wherein said insect pests are thrips.

12. A method for improving plant properties including increasing growth rate, increasing nodulation, increasing the percent dry weight of the plant, increasing fresh weight, and improving resistance to pests over the same properties for a wild type plant, comprising contacting the plant with an effective amount of a proline, wherein said proline is selected from the group consisting of 2-hydroxy-5-oxoproline (2-oxoglutaramate), 5-oxoproline (2-pyrrolidone-5-carboxylic acid), and mixture thereof.

13. A method for improving plant properties including increasing growth rate, increasing nodulation, increasing the percent dry weight of the plant, increasing fresh weight, and improving resistance to pests over the same properties for a wild type plant, comprising contacting the plant with an effective amount of a proline or a mixture of prolines, further comprising the steps of screening the plants contacted with an effective amount of the proline or the mixture of prolines for those plants which demonstrate improved properties in response to contact with the effective amount of the proline or the mixture of prolines therewith, and genetically segregating the screened plants, thereby producing strains of plants which exhibit a improved properties in response to contact with the effective amount of the proline or mixture of prolines therewith.

14. A method for improving plant properties including increasing growth rate, increasing nodulation, increasing the percent dry weight of the plant, increasing fresh weight, and improving resistance to insect pests over the same properties for a wild type plant, comprising contacting a plant with an effective amount of a proline or a mixture of prolines, wherein said insect pests are thrips.

* * * * *